United States Patent [19]

Wideman

[11] E Re. 29,766

[45] Reissued Sep. 19, 1978

[54] METHOD OF AND MEANS FOR TREATING BURN VICTIMS

[75] Inventor: Ronald H. Wideman, Menasha, Wis.

[73] Assignee: Poly-Wide, Inc., Menasha, Wis.

[21] Appl. No.: 782,720

[22] Filed: Mar. 30, 1977

Related U.S. Patent Documents

Reissue of:

[64] Patent No.: 3,985,130
Issued: Oct. 12, 1976
Appl. No.: 575,413
Filed: May 7, 1975

[51] Int. Cl.[2] ..... A61B 19/06

[52] U.S. Cl. ..... 128/132 D; 5/334 R; 128/149

[58] Field of Search ..... 128/132 R, 132 D, 149, 128/155; 5/334 R, 334 C

[56] References Cited

U.S. PATENT DOCUMENTS

| | | | |
|---|---|---|---|
| 2,056,767 | 10/1936 | Blath | 128/149 |
| 3,122,142 | 2/1964 | Crowe | 128/296 |
| 3,216,417 | 11/1965 | Posey | 128/149 |
| 3,508,544 | 4/1970 | Moore et al. | 128/149 |
| 3,545,442 | 12/1970 | Wicker et al. | 128/296 |
| 3,619,336 | 11/1971 | Hughes | 5/334 R |
| 3,668,050 | 6/1972 | Donnelly | 128/132 D |

*Primary Examiner*—Lawrence W. Trapp
*Attorney, Agent, or Firm*—Kinzer, Plyer, Dorn & McEachran

[57] ABSTRACT

A method *and means* of treating, burn and decubitus patients in which a generally nonadhering disposable laminated fabric having nonwoven non-migrating fibrous surfaces is interposed between the patient and a surface on which he is supported.

27 Claims, No Drawings

METHOD OF AND MEANS FOR TREATING BURN VICTIMS

Matter enclosed in heavy brackets [ ] appears in the original patent but forms no part of this reissue specification; matter printed in italics indicates the additions made by reissue.

SUMMARY OF THE INVENTION

This invention is directed to a method of treating burn victims and more specifically, to a method for treating and providing custodial care for burn and decubitus patients by interposing between the patient and the surface on which he is supported a nonadhering disposable laminated fabric having nonwoven non-migrating fibrous surfaces.

An object of this invention is a method of treating burn patients which enhances patient comfort.

Another object is a method of treating burn victims which permits air and fluid exchange to burned body tissues.

Another object is a method of treating burn patients in which the patient is insulated from the usual bed coverings and other surfaces which may adhere to his wounds.

Another object is a method of treating burn patients which is practical, economical and conductive to the natural healing process of body tissues.

With more particularly, an object of this invention is a method of treating burn and decubitus patients in which a nonadhering non-migrating fibrous surface supports the patient.

Other objects may be found in the following specification, and claims.

DESCRIPTION

The novel method of this invention is concerned with interposing, between the burn or decubitus patient and a surface which supports him, a disposable laminated fabric which insulates the patient from those surfaces which may tend to infect or adhere to damaged body tissues. Such a method may be accomplished in any number of ways by either covering surfaces with which the patient will come into contact or covering the patient himself. While all such variations come under the principle of the present invention, the method will be described according to common applications in the treatment of burn victims.

To insulate the burned or otherwise damaged tissues of the patient from the usual bed coverings or linens which generally tend to adhere to the patient's wounds, the method of the present invention entails spreading over a bed a generally nonadhering disposable laminated bed sheet having outer layers of a nonwoven non-migrating fibrous rayon and inner layer of polyurethane foam, which inner layer is fastened by an adhesive to the outer layers over their entire extent. The patient is then positioned on the bed in such a manner that burned tissue of the patient's body is in contact only with the laminated bed sheet provided by the method of the present invention. A second sheet of similar material may then be used to at least partially cover the patient for the purpose of covering him to prevent exposure or to further insulate him from contact with usual bed coverings which may be required for warmth.

In the normal course of treatment of a burn victim, it is likely that the patient will come into contact with surfaces other than his own bed. For example, operating tables or other structures provided for special treatment of burn victims may be similarly covered according to the method of this invention. An important point is that the damaged tissue of the patient be protected by interposing between the tissue and any surface which it would contact a generally nonadhering disposable laminated fabric described in connection with the method of this invention.

The aforementioned laminated fabric has an inner core of cellular plastic material having oompressible foam cells and outer layers on opposite sides of the core formed of nonwoven non-migrating fibrous material. The nonwoven outer layers are attached to the inner core of cellular plastic by layers of adhesive.

Specifically, the inner core may be an open cell polyurethane, the outer layers an oriented rayon as described below and the adhesive may be polyvinyl chloride.

The outei rayon layers are comprised of a multitude of rayon fibers longitudinally oriented with respect to the web which they form. The fibers are not woven together, but rather, they are bonded to one another by an acrylic resin applied generally to one entire side of the rayon web. The resultant rayon web thus has a smooth side presenting firmly fixed nonwoven rayon fibers and a rougher side revealing the loose fiber ends. It is essential feature of the laminated fabric that the smooth side of the rayon layers be directed outwardly so that the free ends of the fibers wick inwardly toward the adhesive in which they are fixed. Thus, outward migration of individual fibers which would tend to adhere to damaged body tissues of the patient is prevented and a nonadhering surface is presented to the patient.

To manufacture the disposable laminated fabric, a web of the nonwoven rayon is unwound from a roll and passed over a roller which applies an adhesive to the rougher sde of the rayon web.

A web of an open cell polyurethane which is slightly wider than the rayon web is unrolled from a second roller at a speed slightly slower than that at which the rayon is advanced. The polyurethane web is passed through subsequent rollers which increase its speed to that of the rayon web, thereby slightly stretching the polyurethane longitudinally which produces a consequent slight reduction in width to that of the thinner rayon web. One purpose of stretching the inner foam layer, on the order of ten percent, is to present a smooth taut surface for attachment by the rayon fibers of the outer layers. The foam web is then brought into contact with the adhesive coated side of the rayon web as they are passed together through heated variable pressure rollers.

A second web of longitudinally oriented nonwoven rayon is advanced from a second roll and passed over another roller which applies adhesive to its rougher side. The second adhesive coated rayon web is then brought into contact with the exposed surface of the polyurethane and run between further heated variable pressure rollers from which the three part laminate web results.

Thus the laminate consists of a slightly stretched inner open cell foam polyurethane core and outer unstretched nonwoven fabric layers adhered to the foam core by layers of adhesive. No further operations are necessary as may be required for other laminate fabric structures wherein substantial elasticity or stretchability are essential characteristics.

To enhance patient comfort during treatment and custodial care, the resulting laminate has a highly resilient surface. The inherent cushioning effect of the foam inner layer certainly contributes to this resiliency. But it is also partially due to the slight relaxation of the inner foam polyurethane core which was slightly stretched during assembly of the laminate fabric. Although the relaxation is not sufficient to impart a readily noticeable elasticity to the fabric or to cause deep wrinkles in the laminate, a certain resiliency is thereby imparted to the finished fabric. Likewise, although the smooth surface of the outer rayon web layers is generally maintained, a gentle waveiness is apparent in the resultant laminate surface which further contributes to the smooth resilient surface presented to the damaged tissue of the burn victim.

In some cases, burns may cover such a large percentage of the patient's body surface that some burned tissue is necessarily engaged against the laminate sheeting on which the patient is positioned. The laminate fabric described above permits the natural healing of such tissue because it its inherent high permeability which results in excellent air and fluid exchange to the damaged tissue. The fabric acts as a sponge for removing fluids from the body tissue. The fluid is passed through the fabric and collected in the mattress pad or underlying bed covering so as to be generally removed from the patient. This is because the rayon is nonabsorbent and so also is the foam. Liquid collects in the voids of the foam but not in the body of the polyurethane foam itself.

An essential characteristic of the laminated fabric, which contributes to the beneficial treatment provided by the method of the present invention, is its nonadherence to the patient's body tissues. This is necessary so that the sheeting may be placed against, over or under severely burned or otherwise damaged body tissues without sticking or imparing the healing process. Nonadherence is largely due to the fact that the rayon fibers do not migrate since the outer surface of the laminate presents firmly fixed rayon fibers which are bound together by a resin. The free ends of the fibers generally wick inwardly to contact the adhesive and thereby prevent outward migration of the fiber ends which would tend to adhere to the patient's tissue.

It will be apparent to those skilled in the art that the method of the present invention has an inherent versatility which goes beyond only insulating a burn victim from a bed surface. For example, footwear or loose fitting garments such as capes or ponchos may be provided and fitted onto burn patients for their comfort and protection when not confined to recovery in bed.

Thus it is apparent that there has been provided, in accordance with the invention, a method of treating and providing custodial care for burn and decubitus patients that wholly satisfies the objects, aims and advantages set forth above. It is evident that many alternatives, modifications and variations will be apparent to those skilled in the art in light of the foregoing description. Accordingly, it is intended to embrace all such alternatives, modification, and variations as fall within the spirit and broad scope of the appended claims.

I claim:

1. A method of treating and providing custodial care for burn and decubitus patients comprising interposing between a patient and a surface on which he is supported a generally nonadhering disposable laminated fabric having outer layers of nonwoven non-migrating fibrous material and an inner layer of foam material therebetween fastened by an adhesive to the outer layers over their entire extent.

2. The method of claim 1 wherein interposing a nonadhering fabric comprises spreading a sheet of said fabric over a bed on which the patient is to be positioned and thereby substantially covering the bed.

3. The method of claim 2 further comprising positioning the patient on the sheet of said fabric.

4. The method of claim 2 further comprising providing a second sheet of said fabric for covering the patient to be positioned on the bed.

5. The method of claim 1 wherein interposing a nonadhering fabric comprises providing for the patient footwear fabricated of said fabric.

6. The method of claim 5 further comprising fitting the footwear onto a foot of the patient.

7. The method of claim 1 wherein interposing a nonadhering fabric comprises providing for the patient loose fitting garments fabricated of said fabric.

8. The method of claim 7 further comprising fitting the garments onto the patient.

9. The method of claim 1 in which said outer layers of nonwoven, non-migrating fibrous material have outer surfaces of nonwoven fibers bonded to one another by a resin.

10. The method of claim 9 in which said nonwoven, nonmigrating fibers of said outer layers are rayon and said resin is an acrylic resin.

11. The method of claim 10 in which said foam material is an open cell polyurethane.

12. The method of claim 10 in which said adhesive is polyvinyl chloride.

13. A bedsheet for use by burn and decubitus patients comprising a generally nonadhering disposable laminated fabric having outer layers of nonwoven, nonmigrating fibrous material and an inner layer of foam material therebetween fastened by an adhesive to the outer layers over their entire extent.

14. The bedsheet of claim 13 in which said outer layers of nonwoven, non-migrating fibrous material have outer surfaces of nonwoven fibers bonded to one another by a resin.

15. The bedsheet of claim 14 in which said nonwoven non-migrating fibers of said outer layers are rayon and said resin is an acrylic resin.

16. The bedsheet of claim 15 in which said foam material is an open cell polyurethane.

17. The bedsheet of claim 15 in which said adhesive is polyvinyl choloride.

*18. A method of treating and providing custodial care for burn and decubitus patients comprising interposing between a patient and a patient supporting surface a generally non-adhering disposable laminated fabric having an outer layer of nonwoven, non-migrating fibrous material which contacts the patient and a backing layer of foam material fastened to the fibrous material by an adhesive.*

*19. The method of claim 18 in which said outer layer of nonwoven, non-migrating fibrous material has an outer surface of nonwoven fibers bonded to one another by a resin.*

*20. The method of claim 18 in which said nonwoven, non-migrating fibers of said outer layer are rayon and said resin is an acrylic resin.*

*21. The method of claim 18 in which said foam material is an open cell polyurethane.*

*22. The method of claim 18 in which said adhesive is polyurethane chloride.*

*23. A bedsheet for use by burn and decubitus patients comprising a generally nonadhering disposable laminated fabric having an outer patient engaging layer of nonwoven, non-migrating fibrous material and a backing layer of a foam material fastened by an adhesive to the outer fibrous layer.*

*24. The bedsheet of claim 23 in which said outer layer of nonwoven, non-migrating fibrous material has an outer surface of nonwoven fibers bonded to one another by a resin.*

*25. The bedsheet of claim 24 in which said nonwoven, non-migrating fibers of said outer patient engaging layer are rayon and said resin is an acrylic resin.*

*26. The bedsheet of claim 25 in which said adhesive is polyvinyl chloride*

*27. The bedsheet of claim 23 in which said foam material is an open cell polyurethane.*

* * * * *